United States Patent
Almond et al.

(10) Patent No.: US 9,006,218 B2
(45) Date of Patent: Apr. 14, 2015

(54) NUCLEOSIDE PHOSPHONATE SALTS

(75) Inventors: Merrick Almond, Apex, NC (US); Bernhard Lampert, Rougemont, NC (US); Ernest Randall Lanier, Chapel Hill, NC (US); Roy W. Ware, Raleigh, NC (US)

(73) Assignee: Chimerix Inc., Durham, NC (US)

( * ) Notice: Subject to any disclaimer, the term of this patent is extended or adjusted under 35 U.S.C. 154(b) by 0 days.

(21) Appl. No.: 13/577,602

(22) PCT Filed: Feb. 14, 2011

(86) PCT No.: PCT/US2011/024774
§ 371 (c)(1),
(2), (4) Date: Oct. 1, 2012

(87) PCT Pub. No.: WO2011/100698
PCT Pub. Date: Aug. 18, 2011

(65) Prior Publication Data
US 2013/0035313 A1    Feb. 7, 2013

Related U.S. Application Data

(60) Provisional application No. 61/304,126, filed on Feb. 12, 2010.

(51) Int. Cl.
| A01N 57/00 | (2006.01) |
| A61K 31/675 | (2006.01) |
| A01N 43/66 | (2006.01) |
| A61K 31/53 | (2006.01) |
| C07D 473/34 | (2006.01) |
| A61K 31/52 | (2006.01) |
| A61K 45/06 | (2006.01) |

(52) U.S. Cl.
CPC .............. *C07D 473/34* (2013.01); *A61K 31/52* (2013.01); *A61K 45/06* (2013.01)

(58) Field of Classification Search
None
See application file for complete search history.

(56) References Cited

U.S. PATENT DOCUMENTS

| 1,944,530 | A | 1/1934 | Schonburg |
| 3,422,021 | A | 1/1969 | Roy |
| 3,468,935 | A | 9/1969 | Peck |
| 4,327,039 | A | 4/1982 | Blum et al. |
| 4,444,766 | A | 4/1984 | Bosies et al. |
| 4,562,179 | A | 12/1985 | Teraji et al. |
| 4,619,794 | A | 10/1986 | Hauser |
| 4,705,651 | A | 11/1987 | Staibano |
| 4,870,063 | A | 9/1989 | Binderup et al. |
| 4,927,814 | A | 5/1990 | Gall et al. |
| 5,043,437 | A | 8/1991 | Khorlin et al. |
| 5,047,533 | A | 9/1991 | Reist et al. |
| 5,142,051 | A | 8/1992 | Holy et al. |
| 5,183,815 | A | 2/1993 | Saari et al. |
| 5,194,654 | A | 3/1993 | Hostetler et al. |
| 5,196,409 | A | 3/1993 | Breuer et al. |
| 5,223,263 | A | 6/1993 | Hostetler et al. |
| 5,247,085 | A | 9/1993 | Harnden et al. |
| 5,300,671 | A | 4/1994 | Tognella et al. |
| 5,300,687 | A | 4/1994 | Schwender et al. |
| 5,312,954 | A | 5/1994 | Breuer et al. |
| 5,395,826 | A | 3/1995 | Naumann et al. |
| 5,411,947 | A | 5/1995 | Hostetler et al. |
| 5,428,181 | A | 6/1995 | Sugioka et al. |
| 5,442,101 | A | 8/1995 | Hanhijarvi et al. |

(Continued)

FOREIGN PATENT DOCUMENTS

| CN | 1810816 | * | 8/2006 |
| CN | 1810816 | A | 8/2006 |

(Continued)

OTHER PUBLICATIONS

"Structure-Activity Relationship and Drug Design," Remington's Pharmaceutical Sciences (Sixteenth Edition). Mack Publishing, 1980, 420-425.*

Berge et al. "Pharmaceutical Salts". Journal of Pharmaceutical Sciences. 66(1); 1977:1-19.*

Painter et al., "Evaluation of Hexadecyloxypropyl-9-R-[2 (Phosphonomethoxy)Propyl]-Adenine, CMX157, as a Potential Treatment for Human Immunodeficiency Virus Type 1 and Hepatitis B Virus Infections," Antimicrob. Agents Chemother. 2007, 51(10):3505, Published Ahead of Print Jul. 23, 2007.*

Kearney et al., "Tenofovir disoproxil fumarate:clinical pharmacology and pharmacokinetics," Clin Pharmacokinet. 2004;43(9):595-612.*

"Creating Orally Available Medicines from Bioactive Molecules." *Presentation at BIG 2004 Annual International Convention.* (Jun. 7, 2004).

Aldern et al. "Increased Antiviral Activity of 1-*O*-Hexadecyloxypropyl-[2-$^{14}$C]Cidofovir in MRC-5 Human Lung Fibroblasts is Explained by Unique Cellular Uptake and Metabolism." *Mol. Pharmacol.* 63.3(2003):678-681.

(Continued)

*Primary Examiner* — Craig Ricci
*Assistant Examiner* — Jared D Barsky
(74) *Attorney, Agent, or Firm* — Cooley LLP; Ivor R. Elrifi; Heidi A. Erlacher

(57) ABSTRACT

The present invention relates to compounds and methods for treating viral diseases. Some compounds of the invention are described by Formula I: (I), wherein $M^+$ is $Na^+$, $Li^+$, $K^+$, $Ca^{2+}$, $Mg^{2+}$, or $NR_cR_dR_eR_f^+$ and $R_c$, $R_d$, $R_e$ and $R_f$ are each independently hydrogen or $C_{1-5}$ alkyl, or a stereoisomer, a diastereomer, an enantiomer or racemate thereof.

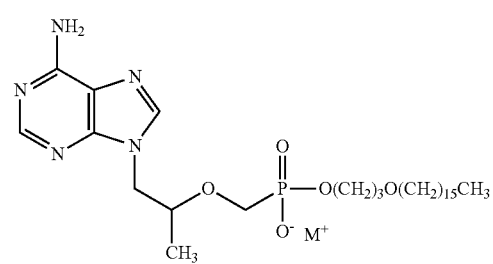

(I)

10 Claims, No Drawings

(56) References Cited

U.S. PATENT DOCUMENTS

| | | |
|---|---|---|
| 5,463,092 A | 10/1995 | Hostetler et al. |
| 5,476,938 A | 12/1995 | Vemishetti et al. |
| 5,484,809 A | 1/1996 | Hostetler et al. |
| 5,484,911 A | 1/1996 | Hong et al. |
| 5,512,671 A | 4/1996 | Piantadosi et al. |
| 5,532,226 A | 7/1996 | Demarest et al. |
| 5,591,852 A | 1/1997 | Vemishetti et al. |
| 5,614,548 A | 3/1997 | Piantadosi et al. |
| 5,627,185 A | 5/1997 | Gosselin et al. |
| 5,650,510 A | 7/1997 | Webb, II et al. |
| 5,656,745 A | 8/1997 | Bischofberger et al. |
| 5,663,159 A | 9/1997 | Starrett, Jr. et al. |
| 5,672,697 A | 9/1997 | Buhr et al. |
| 5,696,277 A | 12/1997 | Hostetler et al. |
| 5,717,095 A | 2/1998 | Arimilli et al. |
| 5,744,461 A | 4/1998 | Hostetler et al. |
| 5,744,592 A | 4/1998 | Hostetler et al. |
| 5,756,711 A | 5/1998 | Zilch et al. |
| 5,760,013 A | 6/1998 | Hwu et al. |
| 5,770,584 A | 6/1998 | Kucera et al. |
| 5,780,617 A | 7/1998 | van den Bosch et al. |
| 5,792,756 A | 8/1998 | Starrett, Jr. et al. |
| 5,798,340 A | 8/1998 | Bischofberger et al. |
| 5,817,638 A | 10/1998 | Hostetler |
| 5,827,831 A | 10/1998 | Hostetler et al. |
| 5,840,716 A | 11/1998 | Ubasawa et al. |
| 5,854,228 A | 12/1998 | Webb, II et al. |
| 5,856,314 A | 1/1999 | Kaas et al. |
| 5,869,468 A | 2/1999 | Freeman |
| 5,877,166 A | 3/1999 | Reist et al. |
| 5,885,973 A | 3/1999 | Papapoulos et al. |
| 5,886,179 A | 3/1999 | Arimilli et al. |
| 5,922,695 A | 7/1999 | Arimilli et al. |
| 5,922,696 A | 7/1999 | Casara et al. |
| 5,935,946 A * | 8/1999 | Munger et al. ................ 514/81 |
| 5,962,437 A | 10/1999 | Kucera et al. |
| 5,977,061 A | 11/1999 | Holy et al. |
| 5,977,089 A | 11/1999 | Arimilli et al. |
| 6,002,029 A | 12/1999 | Hostetler et al. |
| 6,030,960 A | 2/2000 | Morris-Natschke et al. |
| 6,043,230 A | 3/2000 | Arimilli et al. |
| 6,069,249 A | 5/2000 | Arimilli et al. |
| 6,194,388 B1 | 2/2001 | Krieg et al. |
| 6,207,646 B1 | 3/2001 | Krieg et al. |
| 6,218,371 B1 | 4/2001 | Krieg et al. |
| 6,225,292 B1 | 5/2001 | Raz et al. |
| 6,239,116 B1 | 5/2001 | Krieg et al. |
| 6,252,060 B1 | 6/2001 | Hostetler |
| 6,448,392 B1 | 9/2002 | Hostetler et al. |
| 6,562,798 B1 | 5/2003 | Schwartz |
| 6,589,940 B1 | 7/2003 | Raz et al. |
| 6,605,602 B1 | 8/2003 | Vats |
| 6,635,472 B1 | 10/2003 | Lauermann |
| RE38,333 E | 11/2003 | Arimilli et al. |
| 6,670,341 B1 | 12/2003 | Kucera et al. |
| 6,716,825 B2 | 4/2004 | Hostetler et al. |
| 6,818,629 B2 | 11/2004 | Peterson et al. |
| 7,026,469 B2 | 4/2006 | Kucera et al. |
| 7,034,014 B2 * | 4/2006 | Hostetler et al. ............. 514/110 |
| 7,094,772 B2 | 8/2006 | Hostetler et al. |
| 7,098,197 B2 | 8/2006 | Hostetler et al. |
| 7,288,265 B1 | 10/2007 | Rolf |
| 7,390,791 B2 | 6/2008 | Becker et al. |
| 7,452,898 B2 | 11/2008 | Hostetler et al. |
| 7,652,001 B2 | 1/2010 | Hostetler et al. |
| 7,749,983 B2 | 7/2010 | Hostetler et al. |
| 7,790,703 B2 | 9/2010 | Hostetler et al. |
| 8,309,565 B2 | 11/2012 | Hostetler et al. |
| 2003/0211072 A1 | 11/2003 | Carreno-Gomez et al. |
| 2004/0019232 A1 | 1/2004 | Hostetler et al. |
| 2004/0022873 A1 | 2/2004 | Guilford et al. |
| 2004/0071757 A1 | 4/2004 | Rolf |
| 2004/0161398 A1 | 8/2004 | Kucera et al. |
| 2004/0224917 A1 | 11/2004 | Dahl et al. |
| 2004/0259845 A1 | 12/2004 | Kucera et al. |
| 2005/0187192 A1 | 8/2005 | Fleming et al. |
| 2005/0261237 A1 | 11/2005 | Boojamra et al. |
| 2006/0128692 A1 | 6/2006 | Chen et al. |
| 2006/0263355 A1 | 11/2006 | Quan et al. |
| 2007/0003516 A1 | 1/2007 | Almond et al. |
| 2007/0003608 A1 | 1/2007 | Almond et al. |
| 2007/0026056 A1 | 2/2007 | Rolf |
| 2008/0009462 A1 | 1/2008 | Hostetler et al. |
| 2008/0020018 A1 | 1/2008 | Moodley et al. |
| 2008/0161324 A1 | 7/2008 | Johansen et al. |
| 2009/0017448 A1 | 1/2009 | Toth et al. |
| 2009/0087451 A1 | 4/2009 | Buller |
| 2009/0111774 A1 | 4/2009 | Tokars et al. |
| 2010/0173870 A1 | 7/2010 | Hostetler et al. |

FOREIGN PATENT DOCUMENTS

| | | |
|---|---|---|
| CS | 220713 B1 | 4/1983 |
| EP | 0186405 A2 | 7/1986 |
| EP | 0253412 A2 | 1/1988 |
| EP | 0632048 A1 | 1/1995 |
| EP | 0753523 A1 | 1/1997 |
| EP | 0897709 A1 | 2/1999 |
| EP | 1438962 A1 | 7/2004 |
| EP | 1914237 A2 | 4/2008 |
| GB | 1280788 A | 7/1972 |
| JP | 61152694 A | 7/1986 |
| JP | 10029998 A | 2/1998 |
| WO | WO-9105558 A1 | 5/1991 |
| WO | WO-9109602 A2 | 7/1991 |
| WO | WO-9520980 A1 | 8/1995 |
| WO | WO-9602555 A1 | 2/1996 |
| WO | WO-9640088 A1 | 12/1996 |
| WO | WO-9728259 A1 | 8/1997 |
| WO | WO-9816247 A1 | 4/1998 |
| WO | WO-9818810 A1 | 5/1998 |
| WO | WO-9838202 A1 | 9/1998 |
| WO | WO-9840100 A1 | 9/1998 |
| WO | WO-9852581 A9 | 11/1998 |
| WO | WO-9908685 A1 | 2/1999 |
| WO | WO-9855495 B1 | 7/1999 |
| WO | WO-0004032 A1 | 1/2000 |
| WO | WO-9951259 A3 | 1/2000 |
| WO | WO-0006588 B1 | 4/2000 |
| WO | WO-0037477 A1 | 6/2000 |
| WO | WO-0112223 A3 | 9/2001 |
| WO | WO-0021556 A9 | 10/2001 |
| WO | WO-0122990 A3 | 10/2001 |
| WO | WO-0139724 A3 | 10/2001 |
| WO | WO-03049746 A2 | 6/2003 |
| WO | WO-2004062600 A2 | 7/2004 |
| WO | WO-2004112718 A3 | 4/2005 |
| WO | WO-2005087788 A2 | 9/2005 |
| WO | WO-2005121378 A2 | 12/2005 |
| WO | WO-2006066074 A2 | 6/2006 |
| WO | WO-2006076015 A2 | 7/2006 |
| WO | WO-2006110655 A2 | 10/2006 |
| WO | WO-2006110656 A2 | 10/2006 |
| WO | WO-0122972 A9 | 12/2006 |
| WO | WO-2006130217 A2 | 12/2006 |
| WO | WO-2007130783 A2 | 11/2007 |
| WO | WO 2008007392 A2 * | 1/2008 |
| WO | WO-2008033466 A2 | 3/2008 |
| WO | WO-2008118013 A2 | 10/2008 |
| WO | WO-2008133966 A1 | 11/2008 |
| WO | WO-2008133982 A2 | 11/2008 |
| WO | WO-2008144743 A1 | 11/2008 |
| WO | WO-2009094190 A2 | 7/2009 |
| WO | WO-2009094191 A2 | 7/2009 |
| WO | WO-2011001519 A1 | 1/2011 |
| WO | WO-2011017253 A1 | 2/2011 |
| WO | WO-2011053812 A1 | 5/2011 |

OTHER PUBLICATIONS

Andrei et al. "Activities of Various Compounds against Murine and Primate Polyomaviruses." *Antimicrob. Agents Chemother.* 41.3(1997):587-593.

(56) References Cited

OTHER PUBLICATIONS

Annaert et al. "In Vitro, Ex Vivo, and in Situ Intestinal Absorption Characteristics of the Antiviral Ester Prodrug Adefovir Dipivoxil." *J. Pharm. Sci.* 89.8(2000):1054-1062.

Balzarini et al. "Antiretrovirus Activity of a Novel Class of Acyclic Pyrimidine Nucleoside Phosphonates." *Antimicrob. Agents Chemother.* 45.7(2002):2185-2193.

Bartlett et al. "Phase I Trial of Doxorubicin with Cyclosporine as a Modulator of Multidrug Resistance." *J. Clin. Oncol.* 12.4(1994):835-842.

Beadle et al. "Alkoxyalkyl Esters of Cidofovir and Cyclic Cidofovir Exhibit Mutiple-Log Enhancement of Antiviral Activity Against Cytomegalovirus and Herpes Virus Replication in Vitro." *Antimicrob Agents Chemother.* 46.8(2002):2381-2386.

Bell et al. "Antibodies Against the Extracellular Enveloped Virus B5R Proteins are Mainly Responsible for the EEV Neutralizing Capacity of Vaccinia Immune Globulin." *J. Virol.* 325.2(2004):425-431.

Bidanset et al. "Oral Activity of Ether Lipid Ester Prodrugs of Cidofovir against Experimental Human Cytomegalovirus Infection." *J. Infect. Dis.* 190.3(2004):499-503.

Biron. "Antiviral Drugs for Cytomegalovirus Diseases." *Antiviral Res.* 71(2006):154-163.

Blasco et al. "Extracellular Vaccinia Virus Formation and Cell-to-Cell Virus Transmission are Prevented by Deletion of the Gene Encoding the 37,000-Dalton Outer Envelope Protein." *J. Virol.* 65.11(1991):5910-5920.

Bray et al. "Antiviral Prophylaxis of Smallpox." *J. Antimicrob. Chemother.* 54.1(2004):1-5.

Bray. "Pathogenesis and Potential Antiviral Therapy of Complications of Smallpox Vaccination." *Antiviral Res.* 58.2(2003):101-114.

Buller et al. "Efficacy of Oral Active Ether Lipid Analogs of Cidofovir in a Lethal Mousepox Model." *Virol.* 318.2(2004):474-481.

Buller et al. "Efficacy of Smallpox Vaccination in the Presence of Antiviral Drugs, Cidofovir, and Hexadecyoxypropylcidofovir." Antiviral Res. 65.3(2005):A80. (Abstract #72).

Ciesla et al. "Esterification of Cidofovir with Alkoxyalkanols Increases Oral Bioavailability and Diminishes Drug Accumulation in Kidney." *Antiviral Res.* 59.3(2003):163-171.

Connelly et al. "Mechanism of Uptake of the Phosphonate Analog (S)-1-(3-hydroxy-2-phosphonylnnethoxy-propyl)Cytosine (HPMPC) in Vero Cells." *Biochem. Pharma.* 46.6(1993):1053-1057.

Dal Pozzo et al. "In Vitro Evaluation of the Anti-orf Virus Activity of Alkoxyalkyl Esters of CDV, cCDV and (S)-HPMPA." *Antiviral Res.* 75(2007):52-57.

De Clercq et al. "Therapeutic Potential of Nucleoside/Nucleotide Analogues Against Poxvirus Infections." *Rev. Med. Virol.* 14.5(2004):289-300.

De Clercq. "Antiviral Drugs in Current Clinical Use." *J. Virol.* 30.2(2004):115-133.

De Clercq. "Clinical Potential of the Acyclic Nucleoside Phosphonates Cidofovir, Adefovir, and Tenofovir in Treatment of DNA Virus and Retrovirus Infections." *Clin. Microbiol. Rev.* 16.4(2003):569-596.

De Clercq. "The Acyclic Nucleoside Phosphonates from Inception to Clinical Use: Historical Perspective." *Antiviral Res.* 75(2007):1-13.

De Clercq. "Vaccinia Virus Inhibitors as a Paradigm for the Chemotherapy of Poxvirus Infections." *Clin. Microbiol. Rev.* 14.2(2001):382-397.

Denes et al. "Main Adult Herpes Virus Infections of the CNS." *Anti-Infective Therapy.* 3.4(2005):663-678.

Fardis et al. "Case Study: Tenofovir Disoproxil Fumarate: An Oral Prodrug of Tenofovir." vol. *V: Prodrugs: Challenges and Rewards Part 1. Biotechnology, Pharmaceutical Aspects.* 5.20(2007):649-657.

Fisher et al. "Phase I Trial of Etoposide with the Cyclosporine SDZ PSC 833, a Modulator of Multidrug Resistance (MDR)." *Proc. Am Soc. Clin. Oncol.* 12(1994):143 (Abstract #368).

Gauvry et al. "Dealkylation of Dialkyl Phosphonates with Boron Tribromide." *Synthesis.* 4(2001):553-554.

Hammond et al. "Alkylglycerol Prodrugs of Phosphonoformate are Potent in Vitro Inhibitors of Nucleoside-Resistant Human Immunodeficiency Virus Type 1 and Select for Resistance Mutations that Suppress Zidovudine Resistance." *Antimicrob. Agents Chemother.* 45.6(2001):1621-1628.

Hartline et al. "Ether Lipid-Ester Prodrugs of Acyclic Nucleoside Phosphonates: Activity Against Adenovirus Replication in Vitro." *J. Infect. Dis.* 191.3(2005):396-399.

Held et al. "Treatment of BK Virus-Associated Hemorrhagic Cystitis and Simultaneous CMV Reactivation with Cidofovir." *Bone Marrow Transplant.* 26(2000):347-350.

Hillenkamp et al. "Topical Treatment of Acute Adenoviral Keratoconjunctivitis With 0.2% Cidofovir and 1% Cyclosporine." *Arch. Ophthalmol.* 119.10(2001):1487-1491.

Hockova et al. "5-Substituted-2,4-diamino-6-[2-(phosphonomethoxy)ethoxy]pyrimidines-Acyclic Nucleoside Phosphonate Analogues with Antiviral Activity." *J. Med. Chem.* 46.23(2003):5064-5073.

Holy et al. "6[2-(Phosphonomethoxy)alkoxy]pyrimidines With Antiviral Activity." *J. Med. Chem.* 45.9(2002):1918-1929.

Holy et al. "Structure-Antiviral Activity Relationship in the Series of Pyrimidine and Purine N-[2-(2-Phosphonomethoxy)ethyl] Nucleotide Analogues." *J. Med. Chem.* 42.12(1999):2064-2086.

Holy. "Phosphonomethoxyalkyl Analogs of Nucleotides." *Curr. Pharma Des.* 9.31(2003):2567-2592.

Holy. "Simple Method for Cleavage of Phosphonic Acid Diesters to Monoesters." *Synthesis.* 4(1998):381-385.

Hostetler et al. "Enhanced Antiproliferative Effects of Alkoxyalkyl Esters of Cidofovir in Human Cervical Cancers Cells in vitro." *Mol. Cancer Ther.* 5.1(2005):156-159.

Hostetler. "Alkoxyalkyl Prodrugs of Acyclic Nucleoside Phosphonates Enhance Oral Antiviral Activity and Reduce Toxicity: Current State of the Art." *Antiviral Res.* 82.2(2009):A84-A98.

Huggins et al. "Cidofovir Treatment of Variola (Smallpox) in the Hemorrhagic Smallpox Primate Model and the IV Monkeypox Primate Model." *Antiviral Res.* 57.3(2003):A78. (Abstract #127).

Huggins et al. "Orally Active Ether Lipid Prodrugs of Cidofovir for the Treatment of Smallpox." *Antiviral Res.* 53(2002):A66. (Abstract #104).

Huggins et al. "Successful Cidofovir Treatment of Smallpox-Like Disease in Variola and Monkeypox Primate Models." *Antiviral Res.* 62.2(2004):A57-A58. (Abstract #72).

Jacobson. "Treatment of Cytomegalovirus Retinitis in Patients with the Acquired Immunodeficiency Syndrome." *Drug Ther.* 337(1997):105-114.

Jasko et al. "A New Approach to Synthesis of 5'-O-phosphonomethyl Derivatives of Nucleosides and Their Analogues." *Bioorganicheskaya Khimiya.* 20.1(1994):50-54. (English Abstract Only).

Josephson et al. "Polyomavirus-Associated Nephropathy: Update on Antiviral Strategies." *Transpl. Infect. Dis.* 8(2006):95-101.

Keith et al. "Evaluation of Nucleoside Phosphonates and Their Analogs and Prodrugs for Inhibition of Orthopoxvirus Replication." *Antimicrob Agents Chemother.* 47.7(2003):2193-2198.

Keith et al. "Inhibitory Activity of Alkoxyalkyl and Alkyl Esters of Cidofovir and Cyclic Cidofovir Against Orthopoxvirus Replication in Vitro." *Antimicrob. Agents Chemother.* 48.5(2004):1869-1871.

Kern et al. "Enhanced Inhibition of Orthopoxvirus Replication in Vitro by Alkoxyalkyl Esters of Cidofovir and Cyclic Cidofovir." *Antimicrob. Agents Chemother.* 46.4(2002):991-995.

Kern et al. "Oral Treatment of Murine Cytomegalovirus Infections with Ether Lipid Esters of Cidofovir." *Antimicrob Agents Chemother.* 48.9(2004):3516-3522.

Kern. "Pivotal Role of Animal Models in the Development of New Therapies for Cytomegalovirus Infections." *Antiviral Res.* 71(2006):164-171.

Kini et al. "Alkoxy Propane Prodrugs of Foscarnet: Effect of Alkyl Chain Length on in Vitro Antiviral Activity in Cells Infected with HIV-1, HSV-1 and HCMV." *Antiviral Res.* 36.1(1997):43-53.

(56) References Cited

OTHER PUBLICATIONS

Komori et al. "Cytochrome P-450 in Human Liver Microsomes: High-Performance Liquid Chromatographic Isolation of Three Forms and Their Characterization." *J. Biochem.(Tokyo).* 104.6(1988):912-916.
Kornbluth et al. "Mutations in the E9L Polymerase Gene of Cidofovir-Resistant Vaccinia Virus Strain WR are Associated with the Drug Resistance Phenotype." *Antimicrob. Agents Chemother.* 50.12(2006):4038-4043.
Lebeau et al. "Activities of Alkoxyalkyl Esters of Cidofovir (CDV), Cyclic CDV, and (S)-9-(3-Hydroxy-2-Phosphonylmethoxypropyl)Adenine Against Orthopoxviruses in Cell Monolayers and in Organotypic Cultures." *Antimicrob. Agents Chemother.* 50.7(2006):2525-2529.
Lederman. "Progressive Vaccinia in a Military Smallpox Vaccinee—United States 2009." *Center for Disease Control.* May 19, 2009. Web. Retrieved Jan. 1, 2013. http://www.cdc.gov/mmwr/preview/mmwrhtml/mm58e0519a1.html.
Lu et al. "Intraocular Properties of Hexadecyloxypropyl-Cyclic-Cidofovir in Guinea Pigs." *J. Ocul. Pharmacol. Ther.* 21.3(2005):205-209.
Lum et al. "Alteration of Etoposide Pharmacokinetics and Pharmacodynamics by Cyclosporine in a Phase I Trial to Modulate Multidrug Resistance." *J. Clin. Oncol.* 10.10(1992):1635-1642.
Lum et al. "MDR Expression in Normal Tissues." *Hematol. Oncol. Clin. No. Amer.* 9.2(1995):319-336.
Niemi et al. "Bisphosphonate Prodrugs: Synthesis and in Vitro Evaluation of Novel Acyloxyalkyl Esters of Clodronic Acid." *J. Med. Chem.* 42.24(1999):5053-5058.
Painter et al. "Biochemical and Mechanistic Basis for the Activity of Nucleoside Analogue Inhibitors of HIV Reverse Transcriptase." *Curr. Topics Med. Chem.* 4.10(2004):1035-1044.
Painter et al. "Design and Development of Oral Drugs for the Prophylaxis and Treatment of Smallpox Infection." *Trends Biotechnol.* 22.8(2004):423-427.
Parker et al. "Efficacy of Therapeutic Intervention with an Oral Ether-Lipid Analogue of Cidofovir (CMX001) in a Lethal Mousepox Model." *Antiviral Res.* 77.1(2008):39-49.
Portilla et al. "Progressive Multifocal Leukoencephalopathy Treated with Cidofovir in HIV-Infected Patients Receiving Highly Active Anti-Retroviral Therapy." *J. Infect.* 41(2000):182-184.
Quenelle et al. "Oral Treatment of Cowpox and Vaccinia Virus Infections in Mice with Ether Lipid Esters of Cidofovir." *Antimicrob. Agents Chemother.* 48.2(2004):404-412.
Quenelle et al. "Oral Treatment of Cowpox and Vaccinia Virus Infections in Mice with Ether Lipid Esters of Cidofovir." *Antimicrob. Agents Chemother.* 48.2(2004):404-412. Erratum in: *Antimicrob. Agents Chemother.* 48.5(2004):1919.
Quenelle et al. "Synergistic Efficacy of the Combination of ST-246 with CMX001 Against Orthopoxviruses." *Antimicrob. Agents Chemother.* 51.11(2007):4118-4127.
Quimby et al. "Tetrasodium Carbonyldiphosphonate." *J. Org. Chem.* 32.12(1967):4111-4114.
Randhawa et al. "Ether Lipids Ester Derivatives of Cidofovir Inhibit Polyomavirus BK Replication in Vitro." *Antimicrob. Agents Chemother.* 50.4(2006):1564-1566.
Remichkova et al. "Synergistic Combination Effect of Cidofovir and Idoxuridine on Vaccinia Virus Replication." *Antiviral Res.* 65.3(2005):A80-A81. (Abstract #74).
Rogers. "A General Synthesis of Phosphonic Acid Dichlorides Using Oxalyl Chloride and DMF Catalysis." *Tetrahed. Lett.* 33.49(1992):7473-7474.
Saady et al. "Direct Esterification of Phosphonic Acid Salts Using the Mitsunobu Reaction." *Synlett.* 6(1995):643-644.
Schinkel et al. "Multidrug Resistance and the Role of P-glycoprotein Knockout Mice." *Eur. J. Cancer.* 31A.7-8(1995):1295-1298.
Singh et al. "Raltegravir is a Potent Inhibitor of XMRV, a Virus Implicated in Prostate Cancer and Chronic Fatigue Syndrome." *PLoS ONE.* 4.5(2010):e9948.
Smee et al. "A Review of Compounds Exhibiting Anti-Orthopoxvirus Activity in Animal Models." *Antiviral Res.* 57.1-2(2003):41-52.
Smee et al. "Characterization and Treatment of Cidofovir-Resistant Vaccinia (WR Strain) Virus Infections in Cell Culture and in Mice." *Antiviral Chem. Chemother.* 16.3(2005):203-211.
Smee et al. "Effects of Four Antiviral Substances on Lethal Vaccinia Virus (IHD Strain) Respiratory Infections in Mice." *Int. J. Antimicrob. Agents.* 23.5(2004):430-437.
Tam. "Individual Variation in First-Pass Metabolism." *Clin. Pharmacokinet.* 25.4(1993):300-328.
Toth et al. "Hexadcyloxypropyl-Cidofovir, CMX001, Prevents Adenovirus-Induced Mortality in a Permissive, Immunosuppressed Animal Model." *PNAS.* 105.20(2008):7293-7297.
Wan et al. "Alkoxyalkyl Esters of Cidofovir and Cyclic Cidofovir: Effects of Alkyl Chain Length, Unsaturation, and Substitution on the in vitro Antiviral Activity in Cells Infected with HSV-1 and HCMV." *224th ACS National Meeting.* Boston, MA. Aug. 18-22, 2002. (Abstract #MEDI-30).
Wan et al. "Comparison of the Antiviral Activities of Alkoxyalkyl and Alkyl Esters of Cidofovir Against Human and Murine Cytomegalovirus Replication in Vitro." *Antimicrob. Agents Chemother.* 49.2(2005):656-662.
Wan et al. "Dimethylformamide as a Carbon Monoxide Source in Fast Palladium-Catalyzed Aminocarbonylations of Aryl Bromides." *J. Org. Chem.* 67.17(2002):6232-6235.
Wawzonek et al. "Preparation of Long Chain Alkyl Hydroperoxides." *J. Org. Chem.* 25.4(1960):621-623.
Williams-Aziz et al. "Comparative Activities of Lipid Esters of Cidofovir and Cyclic Cidofovir Against Replication of Herpesviruses in Vitro." *Antimicrob. Agents Chemother.* 49.9(2005):3724-3733.
Yang et al. "An Orally Bioavailable Antipoxvirus Compound (ST-246) Inhibits Extracellular Virus Formation and Protects Mice from Lethal Orthopoxvirus Challenge." *J. Virol.* 79.20(2005):13139-13149.
Gallant et al. "Tenofovir disoproxil fumarate (Viread®) for the Treatment of HIV Infection." *Expert Rev. Anti-infect. Ther.* 1.3(2003):415-422.
Postma et al. "Cost-Effectiveness of Antenatal HIV-Testing: Reviewing its Pharmaceutical and Methodological Aspects." *Expert Opin. Pharmacother.* 5.3(2004):521-528.
Cihlar et al. "Design and Profiling of GS-9148, a Novel Nucleotide Analog Active Against Nucleoside-Resistant Variants of Human Immunodeficiency Virus Type 1, and Its Orally Bioavailable Phosphonoamidate Prodrug, GS-9131." *Antimicrob. Agents Chemother.* 52.2(2008):655-665.
Delaney et al. "Combinations of Adefovir with Nucleoside Analogs Produce Additive Antiviral Effects against Hepatitis B Virus in Vitro." *Antimicrob. Agents Chemother.* 48.10(2004):3702-3710.
Fung et al. "Tenofovir Disoproxil Fumarate: A Nucleotide Reverse Transcriptase Inhibitor for the Treatment of HIV Infection." *Clin. Ther.* 24.10(2002):1515-1548.
Myrick et al. "The Triple Combination of Tenofovir, Emtricitabine and Efavirenz Shows Synergistic Anti-HIV-1 Activity in Vitro." *Antiviral Res.* 74. 3(2007): A61. (Abstract #83).

\* cited by examiner

NUCLEOSIDE PHOSPHONATE SALTS

RELATED APPLICATIONS

This application is a national stage application, filed under 35 U.S.C. §371, of International Application No. PCT/US2011/024774, filed on Feb. 14, 2011, which claims the benefit of U.S. Provisional Application No. 61/304,126, filed Feb. 12, 2010, each of which is incorporated by reference herein in its entirety.

BACKGROUND OF THE INVENTION 3-(hexadecyloxy)propyl hydrogen ((R)-1-(6-amino-9H-purin 9-yl) propan-2-yloxy)methylphosphonate; (referred to as CMX157, hexadecyloxypropyl tenofovir or HDP-TFV), a lipid conjugate of tenofovir, was designed to mimic lysophosphatidylcholine to take advantage of natural lipid uptake pathways and to achieve high intracellular concentrations of the active antiviral, with the aim of increasing the effectiveness of tenofovir (TFV) against wild-type and mutant HIV (See Hostetler et al. Enhanced oral absorption and antiviral activity of 1-O-octadecyl-sn-glycero-3-phospho-acyclovir and related compounds in hepatitis B virus infection, in vitro. Biochem Pharmacol 53:1815-22 (1997); Painter et al., Antimicrob. Agents Chemother. 51:3505-9 (2007), and Painter, et al., Trends Biotechnol. 22:423-7 (2004).) In addition, CMX157 may also be used to treat HIV and/or HBV and inhibit the development of resistance to other antiviral compounds. (See PCT Publication Nos. WO 2009/094191 and WO 2009/094190). The structure of CMX157 is shown below:

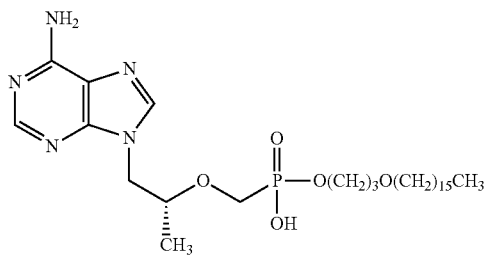

CMX 157

Recent data have indicated that the gammaretrovirus xenotropic murine leukemia virus-related virus (XMRV) and other murine leukemia virus (MLV)-related viruses are associated with prostate cancer and/or chronic fatigue syndrome. (See for example, Schlaberg R et al., PNAS, 106 (38): 6351-6 (2009), and Lombardi V C, et al., Detection of an infectious retrovirus, XMRV, in blood cells of patients with chronic fatigue syndrome, Science, 326 (5952): 585-9, (October 2009), and Lo et al., PNAS early edition, published online before print Aug. 23, 2010, doi: 10.1073/pnas. 1006901107). So far, there is limited medical treatment for prostate cancer and there is no effective treatment for chronic fatigue syndrome. Therefore, there is a need for new drugs that can be used to treat viral diseases.

SUMMARY OF THE INVENTION

A first aspect of the invention provides the compounds having the structure of formula I

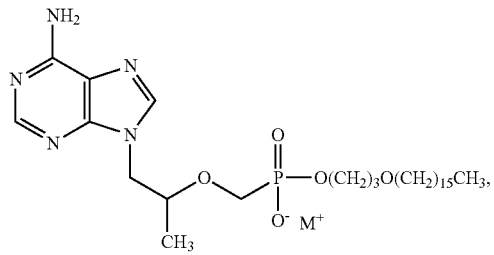

(I)

wherein $M^+$ is $Na^+$, $Li^+$, $K^+$, $Ca^{2+}$, $Mg^{2+}$, or $NR_cR_dR_eR_f^+$ and $R_c$, $R_d$, $R_e$ and $R_f$ are each independently hydrogen or $C_{1-5}$ alkyl, or a stereoisomer, a diastereomer, an enantiomer or racemate thereof. In one embodiment, the compound has the structure of

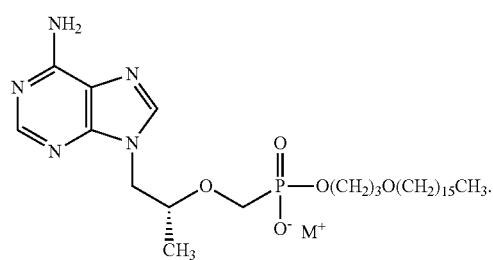

In another embodiment, $M^+$ is $K^+$.

Another aspect of the invention provides pharmaceutical compositions, composition in a dosage form of tablet or capsule, intravenous formulation, solutions, or suspensions comprising the compounds described herein.

A further aspect of the invention provides processes of preparing the compounds described herein. The processes comprise dissolving compound I in a solvent,

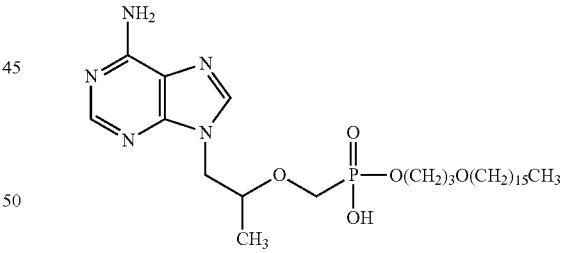

Compound I adding a base to the mixture of the solvent and compound I, and removing the solvent.

Another aspect of the invention provides methods of treating or preventing a viral disease. The methods comprises administering to a subject an effective amount of the compounds described herein (e.g., CMX157 or a compound of formula I). In one embodiment, the virus is a retrovirus, e.g., xenotropic murine leukemia virus-related virus (XMRV).

Another aspect of the invention provides methods of treating or preventing chronic fatigue syndrome. Another aspect of the invention provides methods of treating or preventing prostate cancer.

A further aspect of the invention provides methods of treating a subject infected with at least one retrovirus and the subject has not been administered an antiviral active agent for the retrovirus. The methods comprise administering compounds described herein to the infected subject in an amount effective to treat the viral infection.

Another aspect of the invention provides methods of treating a subject infected with at least one retrovirus and the subject has developed resistance or a toxic response to at least one other antiviral compound in response to prior administration of said at least one other antiviral compound to said subject for the retrovirus infection. The methods comprise administering to the infected subject compounds described herein in an amount effective to treat the viral infection.

A further aspect of the invention provides methods of inhibiting sexual transmission of HIV. The methods comprise topically applying to the skin or epithelial tissue of a human a therapeutically effective amount of a composition comprising an antiviral agent, the compound described herein. The methods further comprise concurrently administering the subject one or more additional antiviral active agents with the compounds described herein.

Another aspect of the invention provides a pharmaceutical composition comprising a compound/salt described herein and a pharmaceutically acceptable carrier. Another aspect of the invention provides a pharmaceutical composition comprising a compound/salt described herein and at least one additional antiviral active agent and a pharmaceutically acceptable carrier.

DETAILED DESCRIPTION OF THE INVENTION

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this invention belongs.

The term "consists essentially of" (and grammatical variants), as applied to the compositions of this invention, means the composition can contain additional components as long as the additional components do not materially alter the composition. The term "materially altered," as applied to a composition, refers to an increase or decrease in the therapeutic effectiveness of the composition of at least about 20% or more as compared to the effectiveness of a composition consisting of the recited components.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

All patents, patent applications and publications referred to herein are incorporated by reference in their entirety. In case of a conflict in terminology, the present specification is controlling.

A. DEFINITIONS

As used herein, "alkali metals" are chemical elements from Group 1 of the periodic table of elements, for example: lithium (Li), sodium (Na), and potassium (K).

Subjects to be treated by the methods of the present invention are, in general, mammalian and primate subjects (e.g., human, monkey, ape, chimpanzee). Subjects may be male or female and may be of any age, including prenatal (i.e., in utero), neonatal, infant, juvenile, adolescent, adult, and geriatric subjects. Thus, in some cases the subjects may be pregnant female subjects. Treatment may be for any purpose, including the therapeutic treatment of previously infected subjects, as well as the prophylactic treatment of uninfected subjects (e.g., subjects identified as being at high risk for infection).

As used herein, "Human immunodeficiency virus" (or "HIV") as used herein is intended to include all subtypes thereof, including HIV subtypes A, B, C, D, E, F, G, and O, and HIV-2.

As used herein, "Hepatitis B virus" (or "HBV") as used herein is intended to include all subtypes (adw, adr, ayw, and ayr) and or genotypes (A, B, C, D, E, F, G, and H) thereof.

As used herein, or "a therapeutically effective amount" refers to an amount that will provide some alleviation, mitigation, and/or decrease in at least one clinical symptom in the subject. Those skilled in the art will appreciate that the therapeutic effects need not be complete or curative, as long as some benefit is provided to the subject.

As used herein, "specificity" or "specifically against" refers to a compound that may selectively inhibit the metabolic activity and/or DNA replication of a certain type of viral infected cells. The specificity may be tested by using any methods known to one skilled in the art, for example, testing $IC_{90}$ and/or $IC_{50}$. In some embodiments, the compounds described herein may have $IC_{90}$ and/or $IC_{50}$ against viral infected cells to be at least about three fold lower than the $IC_{90}$ and/or $IC_{50}$ against normal (uninfected) cells. In some embodiments, the compounds described herein may have $IC_{90}$ and/or $IC_{50}$ against viral infected cells to be about three fold to ten fold lower than the $IC_{90}$ and/or $IC_{50}$ against normal (uninfected) cells. In some embodiments, the compounds described herein may have $IC_{90}$ and/or $IC_{50}$ against viral infected cells to be at least ten fold lower than the $IC_{90}$ and/or $IC_{50}$ against normal (uninfected) cells. In some embodiments, the compounds described herein may have specific cytotoxicity against viral infected and/or transformed cells. The cytotoxicity may be measured by any methods known to one skilled in the art.

Unless otherwise stated, structures depicted herein are meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

As used herein, the term "gamma retrovirus" refers to a genus of the retroviridae family. Examples include, for example, murine leukemia virus, feline leukemia virus, feline sarcoma virus, and avian reticuloendotheliosis virus. Many gamma retroviruses share a conserved RNA structural element, known as a core encapsidation signal.

As used herein, the terms "treatment," "treat," and "treating" refer to reversing, alleviating, inhibiting the progress of a disease or disorder as described herein, or delaying, eliminating or reducing the incidence or onset of a disorder or disease as described herein, as compared to that which would occur in the absence of the measure taken. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein the terms "preventing," "prophylactic" or "prophylaxis" means causing the clinical symptoms of a disease or condition not to develop i.e., inhibiting the onset of a disease or condition in a subject that may be exposed to or predisposed to the disease or condition, but does not yet experience or display symptoms of the disease or condition. Preventative administration means that a compound of the invention is administered to a subject prior to observation of symptoms and/or a suspected exposure to a causative agent of the condition (e.g., a pathogen or carcinogen). Generally, preventative administration may reduce (a) the likelihood that a subject that receives the treatment develops the condition and/or (b) the duration and/or severity of symptoms in the event the subject develops the condition.

Active compounds of the present invention may optionally be administered in combination (or in conjunction) with other active compounds and/or agents useful in the treatment of viral infections as described herein. The administration of two or more compounds "in combination" or "in conjunction" means that the two compounds are administered closely enough in time to have a combined effect, for example an additive and/or synergistic effect. The two compounds may be administered simultaneously (concurrently) or sequentially or it may be two or more events occurring within a short time period before or after each other. Simultaneous administration may be carried out by mixing the compounds prior to administration, or by administering the compounds at the same point in time but at different anatomic sites or using different routes of administration. In some embodiments, the other antiviral agent may optionally be administered concurrently.

"Parenteral" as used herein refers to subcutaneous, intravenous, intra-arterial, intramuscular or intravitreal injection, or infusion techniques.

"Topically" as used herein encompasses administration rectally and by inhalation spray, as well as the more common routes of the skin and mucous membranes of the mouth and nose and in toothpaste.

B. COMPOUNDS

The investigators of the present invention discovered that the free acid form of CMX157 is relatively unstable. (See Example 2) It is surprising to find that the salts of CMX157 are much more stable than CMX157 and possess superior physical properties such as hydroscopicity and handling properties, which make the processing and formulation easier.

In particular, one aspect of the invention provides compounds of formula I

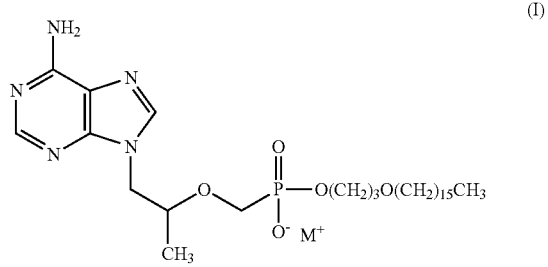

(I)

wherein $M^+$ is potassium ($K^+$), sodium ($Na^+$), lithium ($Li^+$), calcium ($Ca^{2+}$), magnesium ($Mg^{2+}$), or $NR_cR_dR_eR_f^+$ and $R_c$, $R_d$, $R_e$ and $R_f$ are each independently hydrogen or $C_{1-5}$ alkyl (e.g., $NH_4^+$, $NH_3CH_3^+$, $NH_3CH_2CH_3^+$, etc) or a stereoisomer, diastereomer, enantiomer or racemate thereof. For compounds of formula I, when $M^-$ is $Ca^{2+}$ or $Mg^{2+}$, two equivalents of the anion are present to meet the requirement for cation-anion balance. In one embodiment, the compound has the structure of

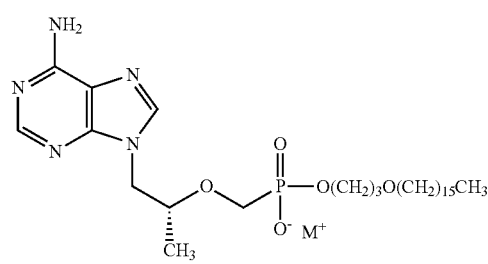

The salt may be in various forms, all of which are included within the scope of the invention. These forms include anhydrous form or solvates. In one embodiment, $M^+$ is $K^+$. In other embodiments, the salt may be crystalline. In one embodiment, the compound is a potassium salt of CMX157.

C. PROCESS OF PREPARATION

In general, the compounds of this invention may be prepared by standard techniques known in the art and by known processes analogous thereto. For example, CMX157 may be prepared in accordance with known procedures, or variations thereof that will be apparent to those skilled in the art. See, e.g., Painter et al., *Antimicrobial Agents and Chemotherapy*

51, 3505-3509 (2007) and US Patent Application Publication No. 2007/0003516 to Almond et al.

General methods for preparing compounds of the present invention are set forth below. In the following description, all variables are, unless otherwise noted, as defined in the formulas described herein. The following non-limiting descriptions illustrate the general methodologies that may be used to obtain the compounds described herein.

In one embodiment, the compound described herein may be prepared by dissolving compound 1 in an appropriate solvent, Compound 1

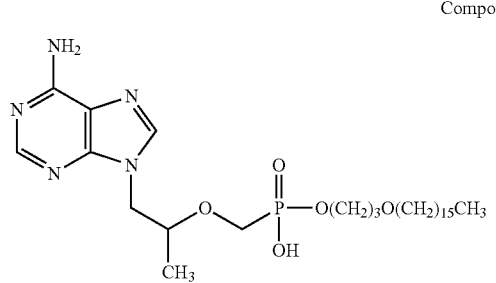

adding a suitable base to the mixture of the solvent and compound 1, and removing the solvent to provide the compound of formula I.

The solvent used in the preparation may be any suitable solvent known to one skilled in the art or a combination of solvents that provides satisfactory yield of the product. In one embodiment, the solvent is a mixture of at least two solvents. Exemplary combination of solvents includes, but is not limited to, dichloromethane and methanol, as well as dichloromethane and ethanol. In one embodiment, the molar ratio of the dichloromethane and methanol is in a range of about 1:1 to 9:1. In one embodiment, the molar ratio of the dichloromethane and methanol is in a range of about 7:3 to 9:1. In a further embodiment, the molar ratio of the dichloromethane and methanol is about 9:1.

The base used in the preparation may be any suitable base known to one skilled in the art or a combination of bases that provides satisfactory yield of the product. In some embodiments, the base is an alkali metal alcoholate base. Exemplary bases include, but are not limited to, potassium methoxide, sodium methoxide, lithium ter-butoxide, ammonium hydroxide, sodium hydroxide, potassium hydroxide, and lithium hydroxide.

The process described herein may further include the step of recrystallization to remove impurity, side products, and unreacted starting material. The recrystallization step comprises the step of dissolving the product in a suitable solvent at an appropriate temperature, cooling to an appropriate temperature for a sufficient period of time to precipitate the compound of formula I, filtering to provide the compounds of formula I. In some embodiments, the temperature for the step of dissolving is in a range of about 50° C. to 80° C.

D. ADDITIONAL ANTIVIRAL AGENTS/COMPOUNDS

Additional antiviral active agents that may be used in carrying out the present invention include HIV-protease inhibitors, nucleoside reverse transcriptase inhibitors (this term herein including nucleotide reverse transcriptase inhibitors), non-nucleoside reverse transcriptase inhibitors, integrase inhibitors, entry inhibitors, fusion inhibitors, maturation inhibitors, and combinations thereof. Numerous examples are known and described in, for example, US Patent Application Publication No. 2006/0234982 to Dahl et al. at Table A therein, and in Table A as set forth below.

Additional examples include, but are not limited to, the integrase inhibitor Isentress or raltegravir (MK-0518: Merck), the CCR5 inhibitor Maraviroc or selzentry (and K-427857, Pfizer) and others of these classes.

Additional examples are provided in U.S. Pat. No. 7,094,413 to Buelow et al.; U.S. Pat. No. 7,250,421 to Nair et al., US Patent Application Publication No. 2007/0265227 to Heneine et al. and US Patent Application Publication No. 2007/0072831 to Cai et al.

The non-nucleoside reverse transcriptase inhibitor ("NNRTI") 6-chloro-4-cyclopropylethynyl-4-trifluoromethyl-1,4-dihydro-2H3,1-benzoxazin-2-one, and pharmaceutically acceptable salts thereof, are described in, for example, U.S. Pat. No. 5,519,021. Examples of the present invention include efavirenz.

The nucleoside reverse transcriptase inhibitor ("NRTI") 2-hydroxymethyI-5-(5-fluorocytosin-1-yl)-1,3-oxathiolane ("FTC") and pharmaceutically acceptable salts thereof, are described in, for example, U.S. Pat. No. 6,642,245 to Liotta et al. Examples of the present invention include emtricitabine.

Integrase inhibitors include, but are not limited to, those described in US Patent Application Publication No. 2007/0072831, WO 02/30426, WO 02/30930, WO 02/30931, WO 02/055079, WO 02/36734, U.S. Pat. No. 6,395,743; U.S. Pat. No. 6,245,806; U.S. Pat. No. 6,271,402; WO 00/039086; WO 00/075122; WO 99/62513; WO 99/62520; WO 01/00578; Jing, et al., Biochemistry, 41, 5397-5403, (2002); Pais, et al., J. Med. Chem., 45, 3184-94 (2002); Goldgur, et al., Proc. Natl. Acad. Sci. U.S.A., 96, 13040-13043 (1999); Espeseth, et al., Proc. Natl. Acad. Sci. U.S.A., 97, 11244-11249, (2000); WO 2005/016927, WO 2004/096807, WO 2004/035577, WO 2004/035576 and US 2003/0055071.

TABLE A 5,6 dihydro-5-azacytidine
5-aza 2'deoxycytidine
5-azacytidine
5-yl-carbocyclic 2'-deoxyguanosine (BMS200,475)
9-(arabinofuranosyl)guanine; 9-(2'-deoxyribofuranosyl)guanine
9-(2'-deoxy-2'-fluororibofuranosyl)-2,6-diaminopurine
9-(2'-deoxy-2'-fluororibofuranosyl)guanine
9-(2'-deoxyribofuranosyl)-2,6-diaminopurine
9-(arabinofuranosyl)-2,6-diaminopurine
Abacavir, Ziagen ®
Acyclovir, ACV; 9-(2-hydroxyethoxylmethyl)guanine
Adefovir dipivoxil, Hepsera ®
Amdoxivir, DAPD
Amprenavir, Agenerase ®
araA; 9-β-D-arabinofuranosyladenine (Vidarabine)
Atazanivir sulfate (Reyataz ®)
AZT; 3'-azido-2',3'-dideoxythymdine, Zidovudine, (Retrovir ®)
BHCG; (+–)-(1a,2b,3a)-9-[2,3-bis(hydroxymethyl)cyclobutyl]guanine
BMS200,475; 5-yl-carbocyclic 2'-deoxyguanosine
Buciclovir; (R) 9-(3,4-dihydroxybutyl)guanine
BvaraU; 1-β-D-arabinofuranosyl-E-5-(2-bromovinyl)uracil (Sorivudine)
Calanolide A
Capravirine
CDG; carbocyclic 2'-deoxyguanosine
Cidofovir, HPMPC; (S)-9-(3-hydroxy-2-phosphonylmethoxypropyl)cytosine
Clevudine, L-FMAU; 2'-Fluoro-5-methyl-(3-L-arabino-furanosyluracil
Combivir ® (lamivudine/zidovudine)
Cytallene; [1-(4'-hydroxy-1',2'-butadienyl)cytosine]
DAPD; (–)-β-D-2,6-diaminopurine dioxolane
ddA; 2',3'-dideoxyadenosine
ddAPR; 2,6-diaminopurine-2',3'-dideoxyriboside TABLE A-continued ddC; 2',3'-dideoxycytidine (Zalcitabine)
ddI; 2',3'-dideoxyinosine, didanosine, (Videx ®, Videx ® EC)
Delavirdine, Rescriptor ®
Didanosine, ddI, Videx ®; 2',3'-dideoxyinosine
DXG; dioxolane guanosine
E-5-(2-bromovinyl)-2'-deoxyuridine
Efavirenz, Sustiva ®
Enfuvirtide, Fuzeon ®
F-ara-A; fluoroarabinosyladenosine (Fludarabine)
FDOC; (−)-β-D-5-fluoro-1-[2-(hydroxymethyl)-1,3-dioxolane]cytosine
FEAU; 2'-deoxy-2'-fluoro-1-β-D-arabinofuranosyl-5-ethyluracil
FIAC; 1-(2-deoxy-2-fluoro-β-D-ababinofuranosyl)-5-iodocytosine
FIAU; 1-(2-deoxy-2-fluoro-β-D-ababinofuranosyl(-5-iodouridine
FLG; 2',3'-dideoxy-3'-fluoroguanosine
FLT; 3'-deoxy-3'-fluorothymidine
Fludarabine; F-ara-A; fluoroarabinosyladenosine
FMAU; 2'-Fluoro-5-methyl-β-L-arabino-furanosyluracil
FMdC
Foscarnet; phosphonoformic acid, PFA
FPMPA; 9-(3-fluoro-2-phosphonylmethoxypropyl)adenine
Gancyclovir, GCV; 9-(1,3-dihydroxy-2-propoxymethyl)guanine
GS-7340; 9-[R-2-[[(S)-[[(S)-1-(isopropoxycarbonyl)ethyl]amino]-phenoxyphosphinyl methoxy]propyl]adenine
HPMPA; (S)-9-(3-hydroxy-2-phosphonylmethoxypropyl)adenine
HPMPC; (S)-9-(3-hydroxy-2-phosphonylmethoxypropyl)cytosine (Cidofovir)
Hydroxyurea, Droxia ®
Indinavir, Crixivan ®
Kaletra ® (lopinavir/ritonavir)
Lamivudine, 3TC, Epivir ™; (2R,5S,cis)-4-amino-1-(2-hydroxymethyl-1,3-oxathiolan-5-yl)-(1H)-pyrimidin-2-one
L-d4C; L-3'-deoxy-2',3'-didehydrocytidine
L-ddC; L-2',3'-dideoxycytidine
L-Fd4C; L-3'-deoxy-2',3'-didehydro-5-fluorocytidine
L-FddC; L-2',3'-dideoxy-5-fluorocytidine
Lopinavir
Nelfinavir, Viracept ®
Nevirapine, Viramune ®
Oxetanocin A; 9-(2-deoxy-2-hydroxymethyl-β-D-erythro-oxetanosyl)adenine
Oxetanocin G; 9-(2-deoxy-2-hydroxymethyl-β-D-erythro-oxetanosyl)guanine
Penciclovir
PMEDAP; 9-(2-phosphonylmethoxyethyl)-2,6-diaminopurine
PMPA, tenofovir; (R)-9-(2-phosphonylmethoxypropyl)adenine
PPA; phosphonoacetic acid
Ribavirin; 1-β-D-ribofuranosyl-1,2,4-triazole-3-carboxamide
Ritonavir, Norvir ®
Saquinavir, Invirase ®, Fortovase ®
Sorivudine, BvaraU; 1-β-D-arabinofuranosyl-E-5-(2-bromovinyl)uracil
Stavudine, d4T, Zerit ®; 2',3'-didehydro-3'-deoxythymidine
Trifluorothymidine, TFT;
Trizivir ® (abacavir sulfate/lamivudine/zidovudine)
Vidarabine, araA; 9-β-D-arabinofuranosyladenine
Viread ®, tenofovir disoproxil fumarate (DF), Bis POC PMPA, TDF; 2,4,6,8-Tetraoxa-5-phosphanonanedioic acid, 5-[[(1R)-2-(6-amino-9H-purin-9-yl)-1-methylethoxy]methyl]-, bis(1-methylethyl)ester, 5-oxide, (2E)-2-butenedioate (1:1)
Zalcitabine, Hivid ®, ddC; 2',3'0dideoxycytidine
Zidovudine, AZT, Retrovir ®; 3'-azido-2',3'-dideoxythymidine
Zonavir; 5-propynyl-1-arabinosyluracil In another embodiment, the compositions of the present invention can include the active compounds as described herein in combination with one or more (e.g., 1, 2, 3) additional active agents described above, in analogous manner as known in the art. For example, combinations of efavirenz (an NRTI), emtricitabine (an NNRTI) and tenofovir DF (an NRTI) are described in, for example, Dahl et al, US Patent Application Publication No. 2007/0099902 to Dahl et al. Specific examples of such combinations include, but are not limited to: compounds described herein in combination with:

(a) FTC/Efavirenz;
(b) 3TC/Efavirenz;
(c) AZT/3TC;
(d) FTC;
(e) 3TC;
(f) FTC/Isentress;
(g) 3TC/Isentress;
(h) PPL-100;
(i) FTC/TMC278;
(k) 3 TC/TMC278;
(l) FTC/TMC125; or
(m) 3TC/TMC125.

E. PHARMACEUTICAL FORMULATION AND ADMINISTRATION

In one embodiment, the present invention is a pharmaceutical composition comprising the compounds described herein. In another embodiment, the pharmaceutical composition further comprises a pharmaceutically acceptable carrier. The term "pharmaceutically acceptable carrier" as used herein refers to any substance, not itself a therapeutic agent, used as a vehicle for delivery of a therapeutic agent to a subject. Examples of pharmaceutically acceptable carriers and methods of manufacture for various compositions include, but are not limited to, those described in Remington's Pharmaceutical Sciences, 18th Ed., Mack Publishing Co. (1990) (See also US Patent Application US 2007/0072831).

The compounds of the invention may be formulated with conventional carriers, diluents and excipients, which will be selected in accord with ordinary practice. Tablets will contain excipients, glidants, fillers, binders, diluents and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose, stearic acid and the like.

Compounds of the invention (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

While it is possible for the active ingredients to be administered alone it is preferably to present them as pharmaceutical formulations. The formulations, both for veterinary and for human use, of the present invention comprise at least one active ingredient, as above defined, together with one or more pharmaceutically acceptable carriers (excipients, diluents, etc.) thereof and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

For infections of the eye or other external tissues e.g. mouth and skin, the formulations are, in some embodiments, applied as a topical ointment or cream containing the active ingredient(s) in an amount of, for example, 0.005 to 20% w/w (including active ingredient(s) in a range between 0.05% and 20% in increments of 0.05% w/w such as 0.6% w/w, 0.65% w/w, 0.7% w/w, etc), in some embodiments, 0.05 to 15% w/w and in other embodiments, 0.05 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. In some embodiments, a hydrophilic emulsifier is included together with a lipophilic emulsifier which acts as a stabilizer. In some embodiments, it includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the present invention include Tween®60, Span®80, cetostearyl alcohol, benzyl alcohol, myristyl alcohol, glyceryl mono-stearate and sodium lauryl sulfate.

The choice of suitable oils or fats for the formulation is based on achieving the desired cosmetic properties, since the solubility of the active compound in most oils likely to be used in pharmaceutical emulsion formulations is very low. In some embodiments, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. In some embodiments, the active ingredient is present in such formulations in a concentration of 0.1 to 20%. In some embodiments, the active ingredient is present in a concentration of 0.1 to 10%. In some embodiments, the active ingredient is present in a concentration of about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents such as pentamidine for treatment of Pneumocystis pneumonia.

Formulations suitable for vaginal administration may be presented as pessaries, rings, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

The present invention further provides veterinary compositions comprising at least one active ingredient as above defined together with a veterinary carrier. Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds described herein may be used to provide controlled release pharmaceutical formulations containing as active ingredient one or more compounds of the invention ("controlled release formulations") in which the release of the active ingredient can be controlled and regulated to allow less frequent dosing or to improve the pharmacokinetic or toxicity profile of a given invention compound. Controlled release formulations adapted for oral administration in which discrete units comprising one or more compounds of the invention can be prepared according to conventional methods. Controlled release formulations may be employed for the treatment or prophylaxis of various microbial infections particularly human bacterial, human parasitic protozoan or human viral infections caused by microbial species including Plasmodium, Pneumocystis, herpes viruses (CMV, HSV 1, HSV 2, VZV, and the like), retroviruses, adenoviruses and the like. The controlled release formulations can be used to treat HIV infections and related conditions such as tuberculosis, malaria, Pneumocystis pneumonia, CMV retinitis, AIDS, AIDS-related complex (ARC) and progressive generalized lymphadeopathy (PGL), and AIDS-related neurological conditions such as multiple sclerosis, and tropical spastic paraparesis. Other human retroviral infections that may be treated with the controlled release formulations according to the invention include Human T-cell Lymphotropic virus and HIV-2 infections. The invention accordingly provides pharmaceutical formulations for use in the treatment or prophylaxis of the above-mentioned human or veterinary conditions and microbial infections.

Pharmacokinetic Enhancers.

The compounds described herein may be employed in combination with pharmacokinetic enhancers (sometimes also referred to as "booster agents"). One aspect of the invention provides the use of an effective amount of an enhancer to enhance or "boost" the pharmacokinetics of a compound of the invention. An effective amount of an enhancer, for example, the amount required to enhance an active compound or additional active compound of the invention, is the amount necessary to improve the pharmacokinetic profile or activity of the compound when compared to its profile when used alone. The compound possesses a better efficacious pharmacokinetic profile than it would without the addition of the enhancer. The amount of pharmacokinetic enhancer used to enhance the potency of the compound is, preferably, subtherapeutic (e.g., dosages below the amount of booster agent conventionally used for therapeutically treating infection in a patient). An enhancing dose for the compounds of the invention is subtherapeutic for treating infection, yet high enough to effect modulation of the metabolism of the compounds of the invention, such that their exposure in a patient is boosted by increased bioavailability, increased blood levels, increased half life, increased time to peak plasma concentration, increased/faster inhibition of HIV integrase, RT or protease and/or reduced systematic clearance. One example of a pharmacokinetic enhancer is RITONAVIR™ (Abbott Laboratories).

F. METHODS OF TREATMENT

In accordance with one aspect of the invention, there are provided methods for treating disorders caused by viral infections. In some aspects of the invention, the virus is a retrovirus. In one embodiment, the virus is a gamma retrovirus. As used herein, "retrovirus" is an RNA virus that is replicated in a host cell via the enzyme reverse transcriptase to produce DNA from its RNA genome. The DNA is then incorporated into the host's genome by an integrase enzyme. The virus thereafter replicates as part of the host cell's DNA. Retroviruses are enveloped viruses that belong to the viral family Retroviridae. Exemplary retroviruses include, but are not limited to, human immunodeficiency virus (HIV) and xenotropic murine leukemia virus-related virus (XMRV). In addition, there is evidence to indicate that XMRV may be related to chronic fatigue syndrome (CFS). (See, e.g., Lombardi, et al., Detection of an infectious retrovirus, XMRV, in blood cells of patients with chronic fatigue syndrome, Science, vol. 326, P 585-589 (October 2009).)

In one embodiment, the compound used to treat the subject is a potassium salt of CMX157. In another embodiment, the compound used to treat the subject is the free form of CMX157.

In one embodiment, the subject is human. In one embodiment, the subject is an immunocompromised and/or an immunosuppressed subject. In some embodiments, the toxic side effects in the immunodeficient subject are decreased compared to the toxic side effects of using tenofovir or other antiviral agents. In one embodiment, the subject is suffering from chronic fatigue syndrome. In one embodiment, the subject is suffering from prostate cancer.

Symptoms of chronic fatigue syndrome (CFS) can include, for example, life-altering fatigue in ordinary activities of daily living, including constellations of syncope, chest pain, muscle aches, palpitations, sore throat, low-grade fevers, inability to exercise without a worsening of all symptoms extending to the following day, cervical lymphadenopathy, cognitive impairment and resultant depression and an intolerance to alcohol. Accompanying intense chronic immune activation can also occur.

In one embodiment, the methods of the present invention alleviate one or more symptoms associated with chronic fatigue syndrome.

As used herein, immunodeficiency (or immune deficiency) is a state in which the immune system's ability to fight infectious disease is compromised or entirely absent. An immunocompromised subject is a subject that has an immunodeficiency of any kind or of any level. Exemplary immunocompromised subject includes, but are not limited to, a subject with primary immunodeficiency (a subject that is born with defects in immune system) and a subject with secondary (acquired) immunodeficiency In addition, other common causes for secondary immunodeficiency include, but are not limited to, malnutrition, aging and particular medications (e.g. immunosuppressive therapy, such as chemotherapy, disease-modifying antirheumatic drugs, immunosuppressive drugs after organ transplants, glucocorticoids). Other exemplary diseases that directly or indirectly impair the immune system include, but are not limited to, various types of cancer, (e.g. bone marrow and blood cells (leukemia, lymphoma, multiple myeloma)), acquired immunodeficiency syndrome (AIDS) caused by human immunodeficiency virus (HIV), chronic infections and autoimmune diseases (e.g. Acute disseminated encephalomyelitis (ADEM), Addison's disease, Alopecia areata, Ankylosing spondylitis, Antiphospholipid antibody syndrome (APS), Autoimmune hemolytic anemia, Autoimmune hepatitis, Autoimmune inner ear disease, Bullous pemphigoid, Coeliac disease, Chagas disease, Chronic obstructive pulmonary disease, Crohns Disease, Dermatomyositis, Diabetes mellitus type 1, Endometriosis, Goodpasture's syndrome, Graves' disease, Guillain-Barré syndrome (GBS), Hashimoto's disease, Hidradenitis suppurativa, Kawasaki disease, IgA nephropathy, Idiopathic thrombocytopenic purpura, Interstitial cystitis, Lupus erythematosus, Mixed Connective Tissue Disease, Morphea, Multiple sclerosis (MS), Myasthenia gravis, Narcolepsy, Neuromyotonia, Pemphigus vulgaris, Pernicious anaemia, Psoriasis, Psoriatic Arthritis, Polymyositis, Primary biliary cirrhosis, Rheumatoid arthritis, Schizophrenia, Scleroderma, Sjögren's syndrome, Stiff person syndrome, Temporal arteritis (also known as "giant cell arteritis"), Ulcerative Colitis, Vasculitis, Vitiligo, Wegener's granulomatosis).

The antiviral activity for CMX157 has been described in U.S. Pat. Nos. 6,716,825, 7,034,014, 7,094,772, 7,098,197, 7,452,898, and PCT publication No. WO 2008/133966, which are incorporated by references in their entireties.

2. Treatment of Privileged Compartment Infections.

It has also been found that compounds described herein may associate or bind to viral particles. Since viral particles migrate or permeate into cellular or tissue compartments that are not generally accessible to active therapeutic agents (thus creating a substantially untreated "reservoir" of infection when subjects are systemically administered such agents), this finding makes possible (a) the treatment of infection in such privileged compartments, and (b) the use of active agents in prophylactic or microbicidal treatments (where association or binding of the active agent to virus before infection occurs is of therapeutic benefit).

In general, a privileged compartment is a cellular or tissue compartment to which said virus permeates in vivo, to which said active agent does not efficiently permeate in vivo in the absence of said virus, and to which said active agent is carried in vivo by said virus when said active agent binds to said virus. For example, when the privileged compartment is a tissue compartment, it may be brain (central nervous system), lymphoid, or testes. Examples of cellular privileged compartments include but are not limited to dendritic cells, microglia, monocyte/macrophages, and combinations thereof. Compositions and methods of treating privileged compartment infections may be prepared and carried out as described above. Prophylactic compositions, devices and methods are discussed in further detail below.

The treatment for privileged compartment infections using CMX157 has been described in PCT Publication Nos. WO 2009/094191 and WO 2009/094190, which are incorporated by references in their entireties.

F. TOPICAL COMPOSITIONS AND MICROBICIDAL METHODS

The present invention can take the form of a topical compositions containing the active agents described herein for inhibiting or combating viral infection, e.g., for prophylactic use. Such compositions (with active agents other than those disclosed herein) are known and described in, for example, U.S. Pat. No. 6,545,007, the disclosure of which is incorporated herein by reference in its entirety.

Such compositions can take several forms. Thus, in one embodiment, the composition is in the form of a cream, lotion, gel, or foam that is applied to the affected skin or epithelial cavity, and preferably spread over the entire skin or epithelial surface which is at risk of contact with bodily fluids. Such formulations, which are suitable for vaginal or rectal administration, may be present as aqueous or oily suspensions, solutions or emulsions (liquid formulations) containing in addition to the active ingredient, such carriers as are known in the art to be appropriate. For "stand-alone" lubricants (i.e., lubricants that are not pre-packaged with condoms), gels and similar aqueous formulations are generally preferred, for various reasons (both scientific and economic) known to those skilled in the art. These formulations are useful to protect not only against sexual transmission of a retrovirus, but also to prevent infection of a baby during passage through the birth canal. Thus the vaginal administration can take place prior to sexual intercourse, during sexual intercourse, and immediately prior to childbirth.

One method of applying an antiviral lubricant to the genitals, for the purposes disclosed herein, involves removing a small quantity (such as a teaspoon, or several milliliters) of a gel, cream, ointment, emulsion, or similar formulation from a plastic or metallic tube, jar, or similar container, or from a sealed plastic, metallic or other packet containing a single dose of such composition, and spreading the composition across the surface of the penis immediately before intercourse. Alternate methods of emplacement include: (1) spreading the composition upon accessible surfaces inside the vagina or rectum shortly before intercourse; and (2) emplacing a condom, diaphragm, or similar device, which has already been coated or otherwise contacted with an antiviral lubricant, upon the penis or inside the vagina. In a preferred embodiment, any of these methods of spreading an anti-viral lubricant across the surfaces of the genitals causes the lubricant to coat and remain in contact with the genital and epithelial surfaces throughout intercourse.

In one embodiment the compositions are used in conjunction with condoms, to enhance the risk-reducing effectiveness of condoms and provide maximum protection for users. The composition can either be coated onto condoms during manufacture, and enclosed within conventional watertight plastic or foil packages that contain one condom per package, or it can be manually applied by a user to either the inside or the outside of a condom, immediately before use.

As used herein, "condom" refers to a barrier device which is used to provide a watertight physical barrier between male and female genitalia during sexual intercourse, and which is removed after intercourse. This term includes conventional condoms that cover the penis; it also includes so-called "female condoms" which are inserted into the vaginal cavity prior to intercourse. The term "condom" does not include diaphragms, cervical caps or other barrier devices that cover only a portion of the epithelial membranes inside the vaginal cavity. Preferably, condoms should be made of latex or a synthetic plastic material such as polyurethane, since these provide a high degree of protection against viruses.

In another embodiment the composition is in the form of an intra-vaginal pill, an intra-rectal pill, or a suppository. The suppository or pill should be inserted into the vaginal or rectal cavity in a manner that permits the suppository or pill, as it dissolves or erodes, to coat the vaginal or rectal walls with a prophylactic layer of the anti-viral.

In still another embodiment the composition is topically applied by release from an intravaginal device. Devices such as vaginal rings, vaginal sponges, diaphragms, cervical caps, female condoms, and the like can be readily adapted to release the composition into the vaginal cavity after insertion.

Compositions used in the methods of this invention may also comprise additional active agents, such as another agent(s) to prevent retrovirus infection, and agents that protect individuals from conception and other sexually transmitted diseases. Thus, in another embodiment, the compositions used in this invention further comprise one or more additional anti-viral agents, virucides effective against viral infections, and/or spermicides.

In one particular embodiment, the composition contains nonoxynol, a widely-used spermicidal surfactant. The resulting composition could be regarded as a "bi-functional" composition, since it would have two active agents that provide two different desired functions, in a relatively inert carrier liquid; the nonoxynol would provide a spermicidal contraceptive agent, and a dihydroalkoxybenzyloxopyrimidine (DABO) derivative would provide anti-viral properties. The nonoxynol is likely to cause some level of irritation, in at least some users; this is a regrettable but is a well-known side effect of spermicidal surfactants such as nonoxynol and octoxynol, which attack and destroy the lipid bilayer membranes that surround sperm cells and other mammalian cells.

The compositions used in this invention may also contain a lubricant that facilitates application of the composition to the desired areas of skin and epithelial tissue, and reduces friction during sexual intercourse. In the case of a pill or suppository, the lubricant can be applied to the exterior of the dosage form to facilitate insertion.

In still another embodiment the invention provides a device for inhibiting the sexual transmission of a retrovirus comprising (a) a barrier structure for insertion into the vaginal cavity, and (b) a composition comprising an active agent as described herein. As mentioned above, preferred devices which act as barrier structures, and which can be adapted to apply the anti-viral agent, include the vaginal sponge, diaphragm, cervical cap, or condom (male or female).

The methods, compositions and devices of this invention can be adapted generally to release active agent in a time sensitive manner that best corresponds to the timing of sexual activity. When topically applied as a lotion or gel, the compositions are preferably applied immediately prior to sexual activity. Other modes of application, such as devices and suppositories, can be designed to release active agent over a prolonged period of time, at a predetermined rate, depending upon the needs of the consumer.

The topical compositions and microbicidal methods using CMX157 have also been described in PCT Publication Nos. WO 2009/094191 and WO 2009/094190, which are incorporated by references in their entireties.

G. EXAMPLES

The present invention will now be described in more detail with reference to the following examples. However, these examples are given for the purpose of illustration and are not to be construed as limiting the scope of the invention.

Example 1

Screening and Preparation of Salts

1. Preliminary Salt Screening

A preliminary salt screening was performed on CMX157. Co-crystal formers were jointly selected from the following list: citric acid, fumaric acid, gentisic acid, hippuric acid, maleic acid, L-mandelic acid, orotic acid, oxalic acid, saccharin, succinic acid, L-tartaric acid, toluenesulfonic acid, ammonia, L-arginine, calcium hydroxide, diethylamine, diethylaminoethanol, ethylenediamine, 1H imidazole, L-lysine, 2-hydroxyethylmorpholine, N-methyl-glucamine, potassium methanolate, zinc tert-butoxide. The salt/co-crystal screening included the evaporation from four solvents followed by the phase equilibration in four further solvents. The solid residues were investigated by Raman microscopy after each experiment.

The comparison of Raman spectra indicated a salt/co-crystal formation in case of gentisate sample (crystalline). The fumarate and hippurate samples were found to be mixtures of crystalline and amorphous material. The detected Raman spectra of these samples indicated a salt formation. The Raman spectra of the following amorphous samples revealed differences to the spectrum of the free drug and that of the corresponding salt former: calcium sample, diethyl amine sample, diethylaminoethanol sample, ethylenediamine sample, imidazole sample, potassium sample. The Raman spectra of L-mandelate and succinate samples revealed only slight differences compared to the spectra of the free drug and that of the corresponding salt former. Investigation of the plate after storage of the plate at r.t. for twelve days resulted partly crystalline material in case of N-methylglucamine, ethylenediamine and imidazole. The recorded Raman spectra of these samples indicated a possible salt formation.

According to results of the preliminary screening, further crystallization optimization was conducted for the following salts: gentisate sample, fumarate sample, hippurate sample, ethylendiamine sample, imidazole sample, N-methylglucamine sample, potassium sample, and succinate sample.

2. Preparation of the Salts

The free acid form of CMX157 may be prepared by methods known to one skilled in the art (See e.g., Painter et al., Antimicrob Agents Chemother 51:3505-9 (2007), and Painter, et al., Trends Biotechnol 22:423-7 (2004).)

CMX157 Sodium Salt:

(55.0 grams, 96.5 mmol) of free acid form of CMX157 was dissolved in a solution of DCM:MeOH (9:1, 550 mL) at room temperature. Sodium methoxide (0.5M solution in methanol, 193.1 mL, 96.5 mmol) was added to the solution and stirred at room temperature for 30 minutes. The reaction mixture was concentrated in vacuo to dryness (50° C. water bath). The resulting off-white foam was dissolved in ethanol (200 mL) at 60° C., diluted with acetone (200 mL), cooled to room temperature, and aged for 18 hours. The suspension was held at 5° C. for 48 hours, filtered, washed with acetone (200 mL), and dried in vacuo at 35° C. for 48 hours to yield CMX157-sodium salt 54.4 g (95.2%) as a white solid. HPLC (AUC) purity 99.6%.

CMX157 Potassium Salt:

(55.0 grams, 96.5 mmol) of free acid form of CMX157 was dissolved in a solution of DCM:MeOH (9:1, 550 mL) at room temperature. Potassium methoxide (25% solution in methanol, 28.5 mL, 96.5 mmol) was added to the solution and stirred at room temperature for 30 minutes. The reaction mixture was concentrated in vacuo to dryness (50° C. water bath). The resulting off-white foam was dissolved in ethanol (200 mL) at 60° C., diluted with acetone (200 mL), cooled to room temperature, and aged for 18 hours. The suspension was held at 5° C. for 48 hours, filtered, washed with acetone (200 mL), and dried in vacuo at 35° C. for 48 hours to yield CMX157-potassium salt 48.4 g (82.4%) as a white solid. HPLC (AUC) purity 97.4%.

CMX157 Lithium Salt:

(55.0 grams, 96.5 mmol) of free acid form of CMX157 was dissolved in a solution of DCM:MeOH (9:1, 550 mL) at room temperature. Lithium tert-butoxide (7.73 g, 96.5 mmol) was added to the solution and stirred at room temperature for 30 minutes. The reaction mixture was concentrated in vacuo to dryness (50° C. water bath). The resulting off-white solid was dissolved in ethanol (800 mL) at 70° C., cooled to room temperature, and aged for 16 hours. The fine suspension was filtered, washed with acetone (200 mL), and dried in vacuo at 35° C. for 48 hours to yield CMX157-lithium salt 51.2 g (92.1%) as a white solid. HPLC (AUC) purity 95.7%.

CMX157 Ammonium Salt:

(55.0 grams, 96.5 mmol) of free acid form of CMX157 was dissolved in 2-propanol (220 mL) at 78° C. in the presence of ammonium hydroxide (28-30%) solution 13.54 mL, 96.5 mmol). The reaction mixture was cooled to room temperature, and aged for 18 hours. The suspension was held at 5° C. for 48 hours, filtered, and air dried for approximately 48 hours to yield CMX157-ammonium salt 51.7 g (91.3%) as a white solid. HPLC (AUC) purity 98.7%.

Example 2

Properties of the Salts

1. Stability of CMX157 and CMX157 Salts

Stability testing was performed for CMX157 and its salts to investigate the quality of the compound over time under various environments. Accelerated conditions were established using an Isotemp Vacuum Oven set at either 40° C. or 60° C. If high humidity was needed, a saturated solution of sodium chloride created an air state containing about 75% humidity.

For determining the amount of CMX157 present in the samples within the stability study, a reference standard of a known purity was used. The reference standard has been shown to be stable under room temperature and accelerated conditions. For analysis, 40 mg of samples and standards are dissolved in 100.0 mL diluent (80 $H_2O$: 20 Methanol: 2 $NH_4OH$). Separation of the drug substance and impurities was achieved using a mobile phase gradient (Table 1) on a Shimadzu A20 HPLC with a Phenomenex Synergi Polar RP 4µ 150×3 mm column. By comparing the areas for the samples at wavelength of 259 nM (kmax) to that of the reference standard, the percentage of CMX157 was determined.

TABLE 1

| The mobile phase gradient for HPLC | | | |
|---|---|---|---|
| Time (min) | % 50 mM Ammonium Acetate with 50 µM EDTA | % Methanol | Flow Rate (mL/min) |
| 0.00 | 35 | 65 | 0.8 |
| 12.00 | 20 | 80 | 0.8 |
| 18.00 | 5 | 95 | 0.8 |
| 18.01 | 35 | 65 | 0.8 |
| 22.00 | end | end | 0.8 |

The stability for CMX157 and various salts of CMX157 under different conditions is summarized in Table 2. As shown in Table 2, about 30% of the free acid decomposes after being placed at 60° C. for 4 weeks (28 days). In contrast, the sodium, potassium, lithium and ammonium salts of the CMX157 have maintained stability under room temperature or at 40° C. after 2 weeks or 4 weeks.

TABLE 2

| Stability for various salts for CMX157 | | | | |
|---|---|---|---|---|
| CMX157 Type | | | | |
| Free Acid | Initial: | | 94.5% | |
| | | 40/75 | | 60° C. |
| | 9 days | 91.5% | | 81.4% |
| | 4 week | 93.9% | | 70.2% |
| $Na^+$ | Initial: | | 99.6% | |
| | | RT | | 40/75 |
| | 2 week | 95.5% | | 96.9% |
| | 4 week | 99.5% | | 99.9% |
| $K^+$ | Initial | | 97.4% | |
| | | RT | | 40/75 |
| | 2 week | 98.3% | | 98.2% |
| | 4 week | 99.6% | | 99.4% |
| $Li^+$ | Initial: | | 95.7% | |
| | | RT | | 40/75 |
| | 2 week | 97.1% | | 97.3% |
| | 4 week | 97.5% | | 99.0% |
| $NH_4^+$ | Initial: | | 98.7% | |
| | | RT | | 40/75 |
| | 2 week | 98.9% | | 98.5% |
| | 4 week | 100.3% | | 101.6% |

Reference: LJK017 p. 136, 139, 148, 152, 157, 160

2. Hygroscopicity for the Salts

According to the observation of the investigators of the present invention, the potassium salt for CMX157 is less hygroscopic than other salts.

3. Processability for the Salts

According to the observation of the investigators of the present invention, the potassium salt for CMX157 is less sticky comparing to other salts during the filtration process.

Example 3

Anti-XMRV Evaluation of CMX157

The following example demonstrates the results of the in vitro anti-xenotropic murine retrovirus (XMRV) evaluations of CMX157 in parallel with tenofovir and other antiviral agents. The test materials were evaluated in PG-4 cells against XMRV collected from the cell-free supernatant of 22Rv1 prostate cancer cells using a complete dose response curve. The experimental details and results are discussed below.

1. Compounds

Test materials (CMX157 $K^+$ salt and Tenofovir) were solubilized at 40 mM and 10 mM in water, respectively, and stored at −20° C. Test materials were evaluated using a 1 µM high test concentration and serially diluted in half-log increments for the in vitro antiviral assay (SOW104-11-01). A second assay was performed (SOW104-11-02) using a 1 µM high test concentration for CMX157, but an increased high test concentration of 100 µM for tenofovir. Ribavirin was purchased from Sigma and used as a positive control compound. AZT and indinavir were obtained from the NIH AIDS Repository and used as additional control compounds.

2. Anti-XMRV Cytoprotection Assay (1) Cell Preparation

PG-cells (ATCC# CRL-2032; feline astrocytes) were passaged in T-75 flasks in McCoy's 5A medium supplemented with 10% heat inactivated fetal bovine serum, 2 mmol/L L-glutamine, 100 U/ml penicillin and 100 µg/ml streptomycin prior to use in the antiviral assay. On the day preceding the assay, cells were split 1:2 to assure they were in an exponential growth phase at the time of infection. Total cell and viability quantification were performed using a hemocytometer and Trypan Blue dye exclusion. Cell viability was to be greater than 95% for the cells to be utilized in the assay. The cells were resuspended at $5\times10^4$ cells per ml (SOW104-11-01) or $1\times10^5$ cells per mL (SOW104-11-02) in tissue culture medium and added to flat bottom microtiter plates in a volume of 100 µl for overnight incubation at 37° C./5% $CO_2$.

(2) Compound Dilution

Serial half-log dilutions were performed. Media was removed from the cell monolayer and 100 µL of 2× concentrations of compound-containing media (DMEM supplemented with 2% FBS, 2 mmol/L L-glutamine, 100 U/ml penicillin and 100 µg/ml streptomycin for SOW104-11-01 or PG-4 cell culture medium for SOW104-11-02) was transferred to the 96-well microtiter plate. Ribavirin and AZT were evaluated in parallel as control compounds for SOW104-11-01. Indinavir and AZT were evaluated in parallel as control compounds for SOW104-11-02

(3) Virus Preparation

The XMRV virus was collected from the cell-free supernatant of 22Rv1 human prostate cancer cells (ATCC# CRL-2505). A pretitered aliquot of virus was removed from the freezer (−80° C.) and allowed to thaw in a biological safety cabinet. The virus was diluted into 2% FBS assay medium such that the amount of virus added to each well in a volume of 100 µl is the amount determined to yield 85 to 95% cell killing at six days post infection (based on optical density values) for SOW104-11-01. PG-4 cell culture medium was used to dilute virus in a volume of 100 µl is the amount determined to yield 85 to 95% cell killing at six days post infection for SOW104-11-02.

(4) XTT Staining of Microtiter Plates

Inhibition of virus induced cytopathic effects (CPE) was quantified by measuring the reduction of the tetrazolium dye XTT (2,3-bis(2-methoxy-4-nitro-5-sulfophenyl)-5-[(phenylamino)carbonyl]-2H-tetrazolium hydroxide). XTT in metabolically active cells is metabolized by the mitochondrial enzyme NADPH oxidase to a soluble formazan product. XTT solution was prepared daily as a stock of 1 mg/mL in PBS. Phenazine methosulfate (PMS) solution was prepared at 0.15 mg/mL in PBS and stored in the dark at −20° C. XTT/PMS stock was prepared immediately before use by adding 40 µL of PMS per mL of XTT solution. 50 µL of XTT/PMS was added to each well of the plate and the plate incubated for 4 h at 37° C. The 4 h incubation has been empirically determined to be within the linear response range for XTT dye reduction with the indicated numbers of cells for each assay. Adhesive plate sealers were used in place of the lids, the sealed plate was inverted several times to mix the soluble formazan product and the plate was read at 450 nm (650 nm reference wavelength) with a Molecular Devices SpectraMax Plus 384 96 well plate format spectrophotometer.

(5) Data Analysis

Raw data was collected from the Softmax Pro 4.6 software and imported into a Microsoft Excel XLfit4 spreadsheet to analyze (four parameter curve fit analysis) and graph the data. Using Microsoft Excel, $EC_{50}$ and $EC_{90}$ (50% and 90% inhibition of virus replication), $TC_{50}$ and $TC_{90}$ (50% and 90% reduction in cell viability) and a therapeutic index (TI, $TC_{50}/EC_{50}$ and $TC_{90}/EC_{90}$) are provided. The $EC_{50}$, $EC_{90}$, $TC_{50}$ and $TC_{90}$ are expressed means±standard deviation. The significant figure is three digits. Raw data for both antiviral activity and toxicity with a graphic representation of the data are provided in a printout summarizing the individual compound activity.

3. Results (1) Anti-XMRV Evaluations

CMX157 $K^+$ salt and tenofovir were evaluated against XMRV collected from 22Rv1 prostate cancer cells in PG-4 cells using a six concentration dose response curve. The results of the XMRV assays are summarized in Table 3.

The AZT control compound was evaluated in parallel with the submitted test materials and yielded $EC_{50}$ values of 0.8 and 0.07 µM. Increased potency observed in SOW 104-11-02 indicates the increased cell density and use of PG-4 cell culture medium provided superior assay conditions as compared with those used in SOW 104-11-01. Ribavirin and indinavir were also evaluated in parallel with the submitted test materials and yielded $EC_{50}$ values of 10.1 µg/mL and 0.8 µM, respectively, with calculated therapeutic indices of 6.5 and 2.7, respectively.

Tenofovir was inactive up to 1 µM when evaluated in SOW 104-11-01 and CMX157 $K^+$ salt yielded an $EC_{50}$ value of 0.04 µM. A second assay was performed using an increased high test concentration for tenofovir which resulted in an $EC_{50}$ value of 2.4 µM and 0.003 µM for CMX157.

TABLE 3

Activity of Compounds in Anti-XMRV Cytoprotection Assay

| Compound | PG-4/XMRV $EC_{50}$ (µM) | PG-4 $TC_{50}$ (µM) | Therapeutic Index |
|---|---|---|---|
| Ribavirin (µg/mL) | 10.1 | 65.2 | 6.5 |
| IDV (Indinavir) | 0.8 | 2.2 | 2.7 |
| AZT (Retrovir) | 0.8 | >1.0 | >1.2 |
|  | 0.07 | >10.0 | >143.0 |
|  | 0.6 | >1.0 | >15.6 |
| TFV (Tenofovir) | >1.0 | >1.0 | — |
|  | 2.4 | >100.0 | >41.5 |
|  | 2.6 | >100.0 | >38.6 |
| CMX157 | 0.04 | 0.4 | 10.0 |
|  | 0.003 | >1.0 | >333.0 |
|  | 0.06 | 5.9 | 97.8 |

As shown above in Table 3, CMX157 $K^+$ salt demonstrated about 60 to 800-fold greater antiviral activity than tenofovir in PG-4 cells against XMRV collected from 22Rv1 prostate cancer cells.

CMX157 was a potent inhibitor of XMRV in vitro with an $EC_{50}$ approximately 20-fold lower than AZT and 800 fold lower than TFV. Higher $EC_{50}$ values were obtained for all compounds when higher passage PG-4 cells were used.

Example 4

Anti-XMRV Activity in Cells

Table 4 shows data from an anti-XMRV activity assay. Specifically, the anti-XMRV activity assay was completed in LNCaP cells (6 day assay) according to the methods described in *PLoS ONE*, volume 5 (4), April 2010, e9948, pages 1-7.

TABLE 4

Anti-XMRV Activity

| Compound | Anti-XMRV Activity in LNCaP cells (6 day assay) | | Cytotoxicity ($IC_{50}$, μM) LNCaP cells |
|---|---|---|---|
| | $EC_{50}$, μM | $EC_{90}$, μM | |
| AZT | 0.0081 ± 0.011 | 0.055 ± 0.051 | >100 |
| CMX157 | 0.0031 ± 0.0021 | 0.037 ± 0.016 | >100 |
| Tenofovir disoproxil fumarate | 0.029 ± 0.026 | 0.21 ± 0.15 | 87.4 |
| Tenofovir | 4.5 ± 3.8 | 17.4 ± 9.0 | >100 |
| Raltegravir | 0.00054 ± 0.00057 | 0.0032 ± 0.0029 | >100 |

These data show $EC_{50}$ and $EC_{90}$ values for CMX157 which are comparable or superior to other active compounds, such as AZT, tenofovir disoproxil fumarate, tenofovir and raltegravir. The cytotoxicity of CMX157 in LNCaP cells was also tested.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed and that modifications to the disclosed embodiments, as well as other embodiments, are intended to be included within the scope of the appended claims. The invention is defined by the following claims, with equivalents of the claims to be included therein.

What is claimed is:

1. A stable crystalline form of a compound of formula I:

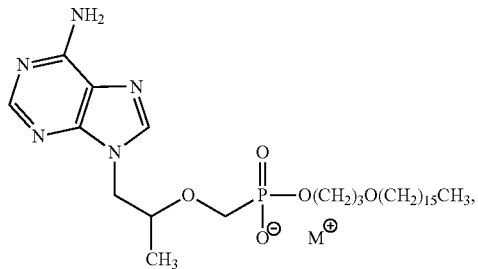

(I)

or a stereoisomer, diastereomer, enantiomer or racemate thereof, wherein $M^+$ is $Na^+$, $Li^+$, $K^+$, $Ca^{2+}$, $Mg^{2+}$, or $NR_cR_dR_eR_f^+$, wherein $R_c$, $R_d$, $R_e$ and $R_f$ are each independently hydrogen or $C_{1-5}$ alkyl, and wherein the crystalline form of the compound is greater than 95% pure and retains greater than 95% purity after being kept at about 40° C. for four weeks.

2. The compound of claim 1 having the structure:

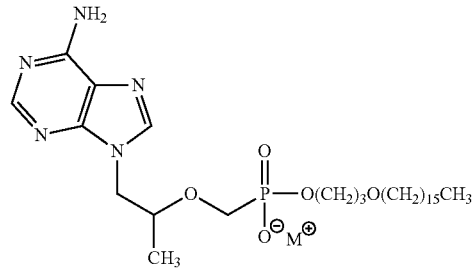

wherein $M^+$ is $Na^+$, $Li^+$, $K^+$, or $NH_4^+$.

3. The compound of claim 2, wherein $M^+$ is $K^+$.

4. A pharmaceutical composition comprising a stable crystalline form of a compound of formula I:

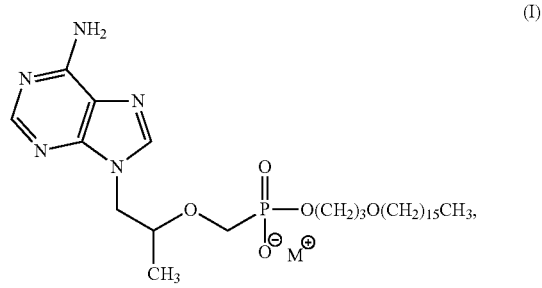

(I)

or a stereoisomer, diastereomer, enantiomer or racemate thereof, and a pharmaceutically acceptable adjuvant, diluent, carrier, or excipient thereof, wherein $M^+$ is $Na^+$, $Li^+$, $K^+$, $Ca^{2+}$, $Mg^{2+}$, or $NR_cR_dR_eR_f^+$, wherein $R_c$, $R_d$, $R_e$ and $R_f$ are each independently hydrogen or $C_{1-5}$ alkyl, and wherein the crystalline form of the compound is greater than 95% pure and retains purity greater than 95% after being kept at 40° C. for about four weeks.

5. The pharmaceutical composition of claim 4, wherein the compound has the structure:

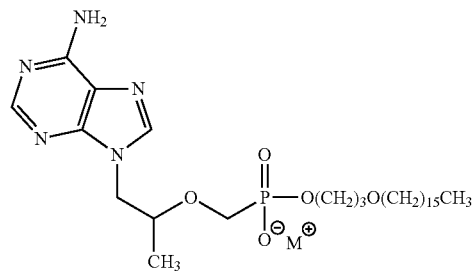

wherein $M^+$ is $Na^+$, $Li^+$, $K^+$ or $NH_4^+$.

6. The pharmaceutical composition of claim 5, wherein $M^+$ is $K^+$.

7. The pharmaceutical composition of claim 5, wherein the compound has purity greater than 96%.

8. The pharmaceutical composition of claim 5, wherein the compound has purity greater than 97%.

9. The pharmaceutical composition of claim 5, wherein the compound has purity greater than 98%.

10. The pharmaceutical composition of claim 5, wherein the compound has purity greater than 99%.

* * * * *